(12) United States Patent
Mimura et al.

(10) Patent No.: US 9,335,335 B2
(45) Date of Patent: May 10, 2016

(54) AUTOMATIC ANALYZER

(71) Applicant: Hitachi High-Technologies Corporation, Tokyo (JP)

(72) Inventors: Tomonori Mimura, Tokyo (JP); Kumiko Kamihara, Tokyo (JP); Isao Yamazaki, Tokyo (JP); Hideto Tamezane, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/422,278

(22) PCT Filed: Jul. 11, 2013

(86) PCT No.: PCT/JP2013/069049
§ 371 (c)(1),
(2) Date: Feb. 18, 2015

(87) PCT Pub. No.: WO2014/034293
PCT Pub. Date: Mar. 6, 2014

(65) Prior Publication Data
US 2015/0219680 A1  Aug. 6, 2015

(30) Foreign Application Priority Data

Aug. 28, 2012  (JP) .................. 2012-188062

(51) Int. Cl.
*G01N 33/00* (2006.01)
*G01N 35/00* (2006.01)
*G01N 35/10* (2006.01)

(52) U.S. Cl.
CPC .... *G01N 35/00623* (2013.01); *G01N 35/00871* (2013.01); *G01N 35/1016* (2013.01); *G01N 2035/00891* (2013.01); *G01N 2035/1018* (2013.01); *Y10T 436/11* (2015.01)

(58) Field of Classification Search
CPC ............... G01N 35/00623; G01N 35/1016; G01N 2035/1018; G01N 35/00871; G01N 2035/00891
See application file for complete search history.

(56) References Cited

U.S. PATENT DOCUMENTS

2010/0327012 A1  12/2010  Saegusa

FOREIGN PATENT DOCUMENTS

| JP | 2002-333449 | 11/2002 |
| JP | 2003-254982 | 9/2003 |
| JP | 2009-216455 | 9/2009 |

OTHER PUBLICATIONS

Translation of JP 2009-216455.*
International Preliminary Report on Patentability received in corresponding International Application No. PCT/JP2013/069049 dated Mar. 12, 2015.
International Search Report in PCT/JP2013/069049, dated Aug. 27, 2013.

* cited by examiner

*Primary Examiner* — Sam P Siefke
(74) *Attorney, Agent, or Firm* — Mattingly & Malur, PC

(57) ABSTRACT

Provided is an automatic analyzer capable of detecting not only clogging and air suction of the dispensation probe but also a decrease in the dispensation quantity caused by a bubble film, air bubbles or a highly viscous sample. Each of a sample/reagent suction operation time and a sample/reagent discharge operation time of a probe is segmented into multiple time sections. For each of the time sections determined by the segmentation, a parameter is calculated by applying a detected pressure waveform to an approximation formula. For each of the time section, the presence/absence of a dispensation abnormality is judged by comparing the calculated parameter with a parameter in cases of normal dispensation. An automatic analyzer capable of judging the presence/absence of an abnormality specific to each time section and making abnormality judgments difficult for conventional techniques can be realized.

6 Claims, 8 Drawing Sheets a) SAMPLE CONTAINER AND PROBE b) RELATIONSHIP BETWEEN SUCTION HEIGHT AND PRESSURE VALUE c) SAMPLE SUCTION PRESSURE WAVEFORM
VARYING WITH SUCTION HEIGHT

FIG. 11
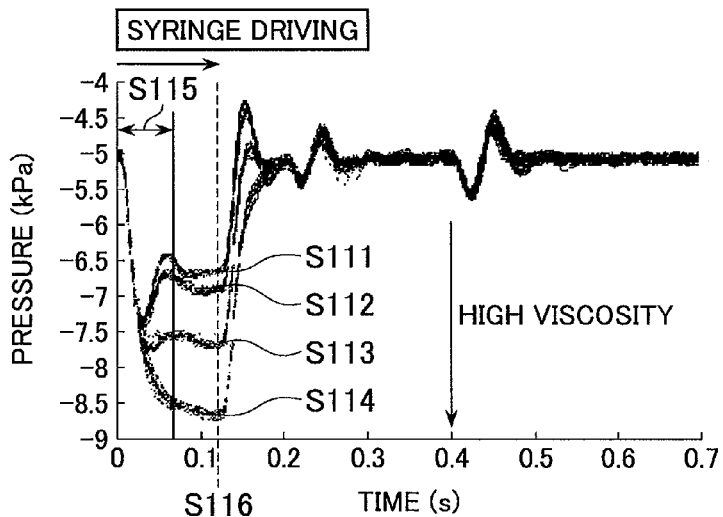
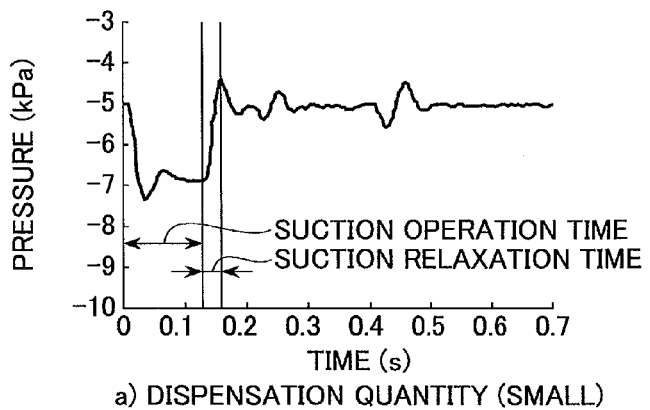
FIG. 12A
a) DISPENSATION QUANTITY (SMALL)
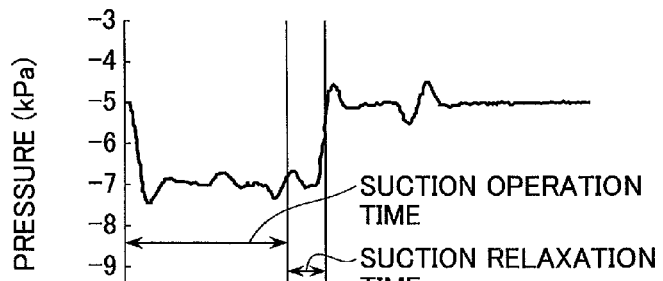
FIG. 12B

AUTOMATIC ANALYZER

TECHNICAL FIELD

The present invention relates to an automatic analyzer for conducting quantitative/qualitative analyses of biological samples such as blood and urine.

BACKGROUND ART

An automatic analyzer discharges a prescribed amount of sample and a prescribed amount of reagent into a reaction cuvette and mixes the sample and the reagent together to cause a reaction. A sample dispensation mechanism of the automatic analyzer is a mechanism for automatically dispensing liquid. For example, the sample dispensation mechanism dispenses a sample, including serum and urine, into a large number of reaction cuvettes in small quantities. The sample dispensation mechanism includes a long and thin probe made of metal or plastic, a tube connected to the probe, and a dispensation syringe arranged at the other end of the tube. The pressure in the tubing is changed by moving a plunger of the dispensation syringe to and fro, by which the sample is suctioned and discharged.

The tubing including the sample probe and the dispensation syringe is usually filled with a liquid (system water), which enables precise suction and discharge of a solution. The diameter of the probe is as small as 0.2 mm to 0.5 mm in order to maintain high dispensation accuracy. Recently, the sample dispensation mechanism is being required to precisely suck in and discharge minute amounts of samples (2 μL or less) and thus the diameter of the sample probe is decreasing further.

High reliability is required of the automatic analyzer as a sample measurement device. The request for high reliability has been met so far by increasing the reliability of the syringe, the dispensation, the channel, or the probe control. Recently, however, not only high reliability but also checking whether the dispensation/discharge operation itself is correctly functioning by use of a pressure sensor or the like is becoming necessary.

It is also being required to issue an alarm after detecting an abnormality in the device control (e.g., clogging of the probe).

For the improvement of reliability, there are two types of technologies: a function of issuing an alarm when an abnormality occurred and a function of checking the amount of a sample/reagent that has been dispensed or sucked in.

As a technology for detection, there is a method of detecting the pressure change in the channel with a pressure sensor and detecting an abnormality by use of the obtained pressure waveform (e.g., in Patent Document 1). This technology is already employed for the detection function of analyzers in order to detect the clogging caused by fibrin, etc. in the samples. In a method for judging whether the clogging has occurred (abnormal state) or not (normal state), the obtained pressure change is recorded and the judgment on abnormality/normality is made on the basis of the distance from normal pressure waveforms by use of the Mahalanobis distance.

While measurement of the dispensation accuracy has been made mainly for samples such as serum and plasma, the objects of the dispensation accuracy measurement are increasing recently, the objects including suction/dispensation of reagents and all samples used.

PRIOR ART DOCUMENT

Patent Document

Patent Document 1: JP-2003-254982-A

SUMMARY OF THE INVENTION

Problem to be Solved by the Invention

Multiple factors such as the viscosity of the sample, formation of bubbles, the height of suction and discharge, and pressure difference can be considered as factors influencing the dispensation accuracy of the automatic analyzer. Above all, it is necessary to check whether the prescribed quantity has actually been dispensed.

In the conventional technology, detection of the clogging of the dispensation probe with fibrin or the like has been the best and sufficient method for the abnormality detection. Detection of total clogging of the dispensation probe is relatively easy since the pressure in the channel changes sharply and greatly when the probe is clogged up with fibrin or the like.

However, when the dispensation accuracy is considered, there are other abnormality factors (other than the clogging with fibrin) related to the dispensation accuracy. For example, factors such as suction/discharge of air bubbles during the sample suction process and mixing of a solution (adhering to the outer surface of the dispensation probe during the suction of the sample) into the reaction cuvette at the time of sample discharge can be assumed to be related to the dispensation accuracy.

Table 1 shows the assumed abnormality factors and corresponding detecting methods by use of the pressure waveform.

TABLE 1

| ABNORMALITY FACTOR OF DISPENSATION ACCURACY DETERIORATION | CHARACTERISTICS OF PRESSURE WAVEFORM | METHOD OF DETECTION FROM PRESSURE WAVEFORM |
| --- | --- | --- |
| PROBE CLOGGING DUE TO FIBRIN OR THE LIKE | SHARP PRESSURE CHANGE DURING SUCTION | DETECT FROM PRESSURE VALUES AT A TIME OF SUCTION |
| SUCTION OF BUBBLE IN SAMPLE OR REAGENT | IRREGULAR PRESSURE FLUCTUATION DURING SUCTION | DETECTABLE IN SOME CASES AS PATTERN CHANGE IN PRESSURE WAVEFORM |
| MIXING OF SOLUTION ADHERING TO OUTER SURFACE OF PROBE | NO PRESSURE CHANGE | UNDETECTABLE |

TABLE 1-continued

| ABNORMALITY FACTOR OF DISPENSATION ACCURACY DETERIORATION | CHARACTERISTICS OF PRESSURE WAVEFORM | METHOD OF DETECTION FROM PRESSURE WAVEFORM |
|---|---|---|
| INTO REACTION CUVETTE | | |
| HIGH VISCOSITY OF SAMPLE OR REAGENT | PRESSURE VALUE DIFFERENCE AND DAMPED OSCILLATION PATTERN CHANGE AT A TIME OF SUCTION | DETECT FROM CORRELATION BETWEEN VISCOSITY AND PRESSURE CHANGE |
| SAMPLING HEIGHT ABNORMALITY | PRESSURE VALUE IN INITIAL STATE | DETECT FROM CORRELATION BETWEEN SUCTION HEIGHT AND PRESSURE VALUE |

As shown in Table 1, the characteristics of the obtained pressure waveform vary depending on the type of the abnormality factor and hence it is impossible to determine the abnormality factor with only one type of discriminant. The method of judging the normality/abnormality also differs among the abnormality factors. Further, in the actual sample dispensation, the number of factors of occurrence of an abnormality is not necessarily one, but multiple abnormalities can occur at the same time. Thus, the method of judging such abnormalities is necessitated to be complicated and it has been impossible to judge whether the dispensation was performed appropriately. Furthermore, judging whether there is an abnormality is difficult in many cases. For example, it is difficult to make the judgment on whether the dispensation was performed appropriately by the conventional judgment method using the Mahalanobis distance.

Abnormal suction and discharge operations and normal suction and discharge operations are not clearly separate; the suction and discharge operation changes continuously in many cases and the boundary between normality and abnormality is sometimes indefinite.

Moreover, after the sample is brought into reaction with multiple reagents, the absorbance of the reaction solution is measured for several minutes in a constant-temperature state (37° C.), and thus approximately 10 minutes of reaction time are necessary. In cases where a dispensation abnormality occurs in the middle of the reaction process, starting the re-measurement would take a long time even if the dispensation abnormality is detected at the instant of occurrence of the abnormality, which deteriorates the efficiency of analysis.

The object of the present invention is to realize an automatic analyzer and a dispensation abnormality judgment method capable of detection of not only clogging and air suction of the dispensation probe but also a decrease in the dispensation quantity caused by a bubble film, air bubbles or a highly viscous sample.

Means for Solving the Problem

To achieve the above object, the present invention is configured as below.

An automatic analyzer includes: a dispensation probe which sucks in a sample or a reagent stored in a sample container or a reagent bottle and discharges the sample or reagent to a reaction cuvette; a pressure detector which detects a pressure in the dispensation probe; an analysis unit which analyzes the sample in the reaction cuvette; an arithmetic processing unit which segments each of the suction operation and the discharge operation of the dispensation probe into multiple time sections, analyzes a pressure waveform detected by the pressure detector in regard to each of the time sections determined by the segmentation, and judges presence/absence of a dispensation abnormality by comparing a result of the analysis of the pressure waveform with a certain criterion; and a display unit which displays the presence/absence of a dispensation abnormality as a result of the judgment by the arithmetic processing unit.

A method for judging dispensation abnormality of an automatic analyzer includes the steps of: sucking in a sample or a reagent stored in a sample container or a reagent bottle and discharging the sample or reagent to a reaction cuvette by use of a dispensation probe; detecting the pressure in the dispensation probe by use of a pressure detector; having an arithmetic processing unit segment each of the suction operation and the discharge operation of the dispensation probe into multiple time sections, analyze a pressure waveform detected by the pressure detector in regard to each of the time sections determined by the segmentation, and judge the presence/absence of a dispensation abnormality by comparing the result of the analysis of the pressure waveform with a certain criterion; and displaying the presence/absence of a dispensation abnormality as the result of the judgment by the arithmetic processing unit.

Advantage of the Invention

According to the present invention, an automatic analyzer and a dispensation abnormality judgment method capable of detection of not only the clogging with fibrin or the air suction of the dispensation probe but also a decrease in the dispensation quantity caused by a bubble film, air bubbles or a highly viscous sample can be realized.

BRIEF DESCRIPTION OF THE DRAWINGS

FIG. 11 is a graph showing pressure waveforms at a time of suction varying depending on sample viscosity.

FIG. 12A is a graph showing a pressure waveform at a time of suction differing in the sample dispensation quantity.

FIG. 12B is a graph showing a pressure waveform at a time of suction differing in the sample dispensation quantity.

MODE FOR CARRYING OUT THE INVENTION

Figure 1:
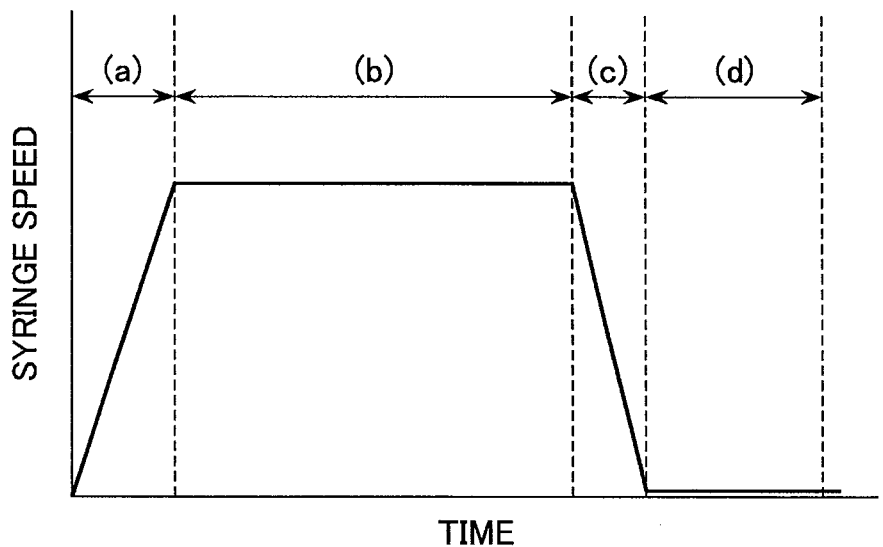
FIG. 1 is a graph showing four sections of a syringe operation process.

With reference to the drawings, a description will now be given of preferred embodiments of the present invention.

Embodiments

Embodiments of the present invention will be explained in detail below with reference to figures.

First Embodiment

Prior to the explanation of the first embodiment of the present invention, the basic idea of the first embodiment will be explained briefly.

In cases where the dispensation abnormality of a sample or a reagent is formed of multiple factors, there would exist two types of relevant information: known information which is already clearly known at the stage of designing the automatic analyzer or determining the analysis parameters and variable information which varies depending on the properties of the sample or the reagent.

An example of the information already clearly known at the stage of designing the automatic analyzer includes the relationship between the dispensation quantity and the driving time of the syringe and the judgment algorithm for detecting the clogging. At the stage of setting the analysis parameters, the type of each sample (such as urine, serum, and whole blood), the position of sampling, the dispensation quantity, the viscosity of each reagent, the presence/absence of a surface active agent, the suction position, the quantity of each reagent, and other information are already known beforehand.

Meanwhile, the variable information which cannot been known beforehand includes the amount of each sample/reagent in each sample/reagent container/bottle, the viscosity of each sample/reagent, and the bubbling tendency of each sample/reagent.

The method for detecting each factor influencing the dispensation accuracy and the method of utilizing the pressure waveform data obtained in the dispensation operation vary from factor to factor. For example, the pressure in the channel at the time of suction and the viscosity of the sample/reagent to be sucked in are in a directly proportional relationship. When the clogging occurs, the pressure value increases to a level close to the level reached when a highly viscous sample/reagent has been sucked in. With the increase in the viscosity of the sample/reagent, the time necessary for the pressure value in the tube (after completion of the suction) to return to the value in the initial state becomes longer. Further, the sample/reagent suction time (syringe driving time) and the amount of the sample/reagent sucked in are proportional. As above, the pressure data fluctuation in the sample/reagent dispensation is caused by a complex combination of multiple factors, and thus determining a single factor of the abnormality is impossible. In cases where the normality/abnormality comparison is made by use of pressure waveforms, even analyzing the pressure waveforms would be impossible in many cases.

The operation of the syringe sucking in and discharging a sample/reagent and the pressure around at times of the suction and the discharge are measured at certain time intervals with the use of a pressure sensor arranged in the middle of a channel connecting the syringe and the probe and the measurement data are stored in a database. Thereafter, in the dispensation of the analyte (sample) and the reagent, the pressure data of the pressure in the channel is analyzed on the basis of the aforementioned known information, and then data analysis of the variable information is performed and abnormality analysis of the suction and dispensation operations is conducted. The procedure for judging whether the sample/reagent suction and discharge operation has been performed normally in the process for analyzing the patient sample includes four processes to be explained below.

It should be noted that each of a sample dispensation mechanism and a reagent dispensation mechanism of the automatic analyzer includes a probe, a syringe, a tube connecting the probe and the syringe, and a pressure sensor connected to the tube. The basic process of the abnormality detection is common to the reagent and the sample.

A method for detecting an abnormality from the measured pressure will be explained below. This detection method is made up of four processes: a pressure measurement process (1), an analysis process (2), a judgment process (3), and an overall judgment process (4).

(1) Pressure Measurement Process

The pressure measurement process is a process for measuring the pressure in the channel and other necessary values by use of detectors.

(2) Analysis Process

In the analysis process, the time domain of the pressure is divided based on information of already-known operation/procedure, such as reagent quantity and sample quantity. The analysis process is a process for analyzing the measured pressure data by applying the pressure data to an approximation formula or the like.

(3) Judgment Process

In the judgment process, abnormality factors are estimated on the basis of parameters calculated in the approximation formula in the process (2) and whether the abnormality is a single abnormality or a complex abnormality is judged on the basis of the pressure values and the parameters calculated in the process (2). The abnormality is examined on the basis of the pressure waveform and existence of an abnormality other than estimated causes is detected.

(4) Overall Judgment

The above three processes (1), (2) and (3) are conducted in the sample dispensation (sampling), the first reagent dispensation and the second reagent dispensation in this order. If an abnormality is detected in an early stage of the analysis process, the subsequent measurement operation will not be carried out. An alarm indicating the abnormality is displayed on the screen of the PC at the stage when the measurement operation has been stopped, or added to the data as a comment.

The analysis process (2) will be described concretely below.

FIG. 1 is a graph for explaining the segmentation of the operation process of the syringe into four sections (a) to (d), the process being used for the suction and the discharge.

The four sections (a) to (d) will be explained below.

The section (a) is a time from a point just after the start of the operation of the syringe till the syringe reaches a constant speed. The section (b) is a time during which the syringe maintains the constant speed. The section (c) is a time from a point when the syringe speed starts decreasing to a point when the syringe stops. The section (d) is a certain length of time after the stoppage of the syringe operation.

Figure 2:
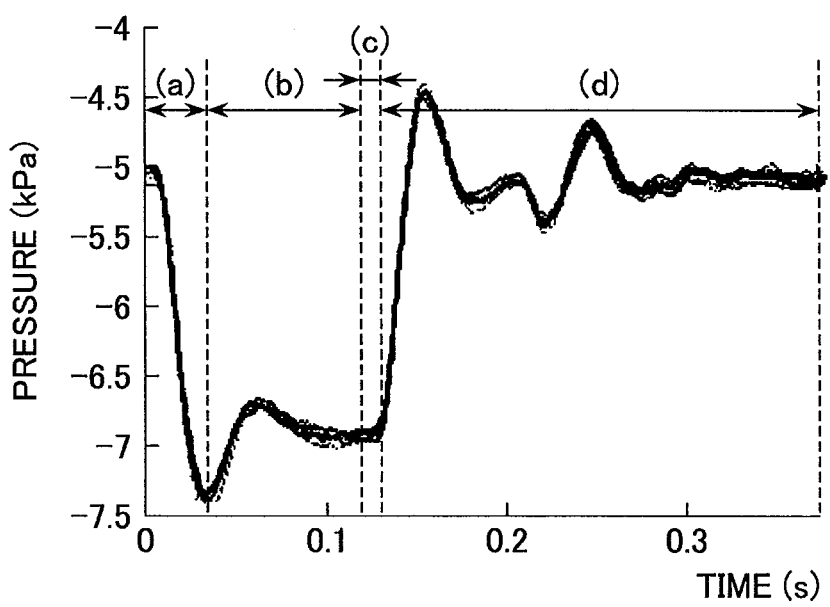
FIG. 2 is a graph showing the relationship between the four sections of the syringe operation process and a pressure waveform at a time of sample suction.
Figure 3:
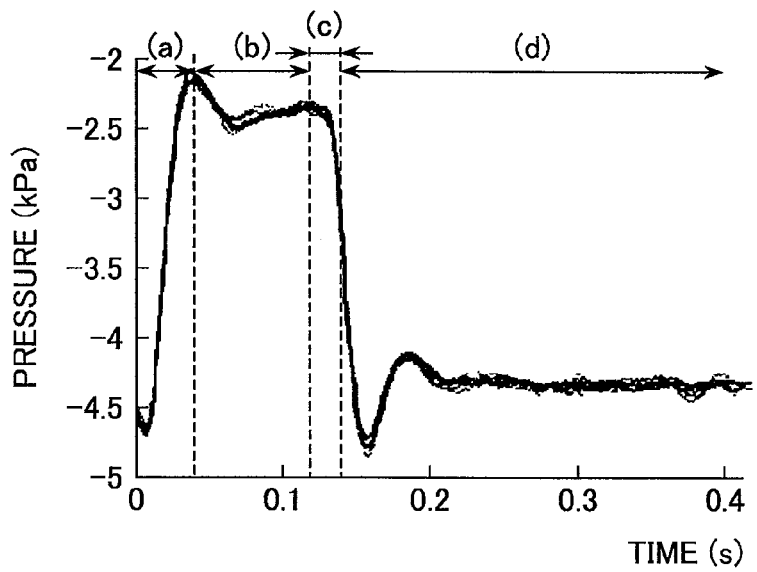
FIG. 3 is a graph showing the relationship between the four sections of the syringe operation process and a pressure waveform at a time of sample discharge.

FIG. 2 is a graph showing an example of the pressure waveform in the four sections (a) to (d) at the time of suction. FIG. 3 is a graph showing an example of the pressure waveform in the four sections (a) to (d) at the time of discharge.

The section (c) is a time for decelerating the syringe speed in consideration of the shear rate in cases of performing the dispensation of a sample/reagent having high viscosity. This section (c) is a relatively short time period.

For the approximation formula to be used for the analysis of each section, the following formulas are used in combination to suit the shape of the pressure waveform.

($\alpha$) Formula in which Pressure Increases with Passage of Time in each Time Domain The exponential function $A+B*\exp(kt)$ can be taken as an example of such a formula. The parameters A, B and k are calculated from the measurement data by means of multiple regression. When B is negative and k is positive, the function indicates that the pressure is decreasing. When the clogging has occurred in the channel, the syringe continues the suction operation for a prescribed amount. Since the actual suction/discharge of the solution is impossible due to the clogging, the pressure in the channel increases or decreases. An exponential curve is a typical example of the pressure change.

($\beta$) Damped Oscillation Function

A function $\sin(\omega t) \times \exp(-kt)$ is an example of a damped oscillation function. The parameters $\omega$ and k are calculated from the measurement data. After high-speed suction/discharge of a solution, even if the syringe is already stopped, the solution itself continues its movement since the solution has certain viscosity. After the stoppage, the pressure in the channel oscillates while gradually decreasing the pressure value. This state is approximated by use of the damped oscillation function.

($\gamma$) Formula for Judging Certain Pressure

A formula Min.$\leq$P$\leq$Max. for judging whether the pressure is within a normal pressure range is used. The minimum permissible value Min. and the maximum permissible value Max. are set on the basis of measurement data obtained previously. When the channel has no clogging and the viscosity of the solution is also low, the channel resistance is low and the pressure change is also small, and thus the pressure in the channel exhibits a constant value.

For each time domain, the analysis is conducted by performing the approximate calculation of the pressure waveform by combining the above three types of formulas or by using one of the three types of formulas. The normality/abnormality judgment can be made by calculating the parameters of the obtained approximation formula(s) and judging the calculated parameters in each time domain.

The judgment process (3) will be now explained concretely below.

The parameters calculated with each approximation formula in the analysis process (2) are utilized. The following parameter is checked in the four time domains determined by the segmentation of the suction/discharge process, that is, in the total of eight time domains determined by the segmentation of the processes.

In each of the four time domains determined by the segmentation, a parameter that can be a factor of an abnormality is checked.

(a) Time from Point just after Start of Operation of Syringe till Syringe reaches Constant Speed For each time domain, the pressure change parameter k calculated from the formula ($\alpha$) in which the pressure increases with the passage of time and the viscosity of the sample are analyzed.

(b) Time during which Syringe Maintains Constant Speed

For each time domain, sampling suction height is analyzed on the basis of the pressure change parameter k calculated from the formula ($\alpha$) in which the pressure increases with the passage of time and a constant pressure value.

(c) Time from Point when Syringe Speed starts Decreasing to Point when Syringe Stops For each time domain, the clogging of the probe is analyzed on the basis of the pressure change parameter k calculated from the formula ($\alpha$) in which the pressure increases with the passage of time.

(d) Certain Length of Time after Stoppage of Syringe Operation

The suction quantity or the discharge quantity is analyzed on the basis of the frequency parameter $\omega$ of the damped waveform.

Figure 4A:
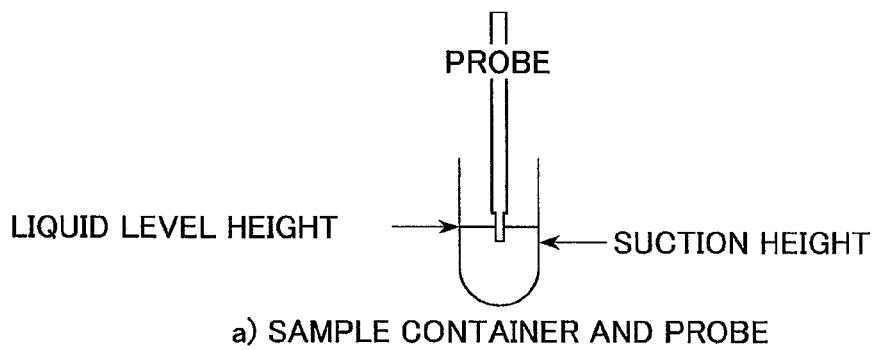
FIG. 4A is a schematic diagram for explaining the relationship between suction height and pressure values.
Figure 4B:
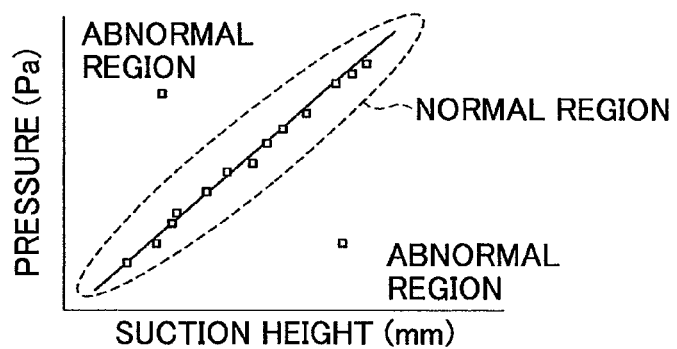
FIG. 4B is a schematic diagram for explaining the relationship between suction height and pressure values.
Figure 4C:
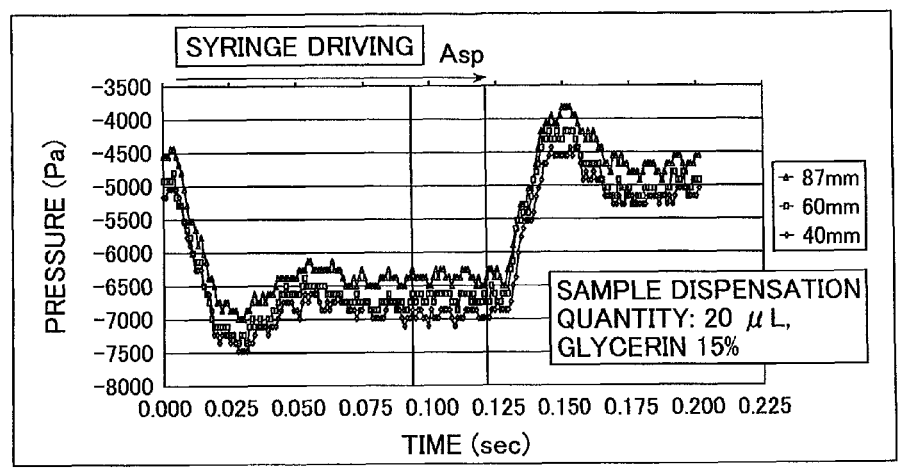
FIG. 4C is a schematic diagram for explaining the relationship between suction height and pressure values.

In order to make the normality/abnormality judgment based on these values, parameter values are previously stored as reference values. In regard to the magnitude of the pressure, the judgment is made on the basis of a relational expression representing the relationship between the pressure and the suction height shown in FIGS. 4A, 4B and 4C.

The overall judgment (4) will now be explained below.

The analysis is carried out in the order of the sampling and the reagent dispensation. Whether the result of the abnormality judgment in the above judgment process (3) is "normal" or "abnormal" is judged in the order of the sampling, the first reagent dispensation and the second reagent dispensation. If an abnormality is detected in the first abnormality judgment about the sampling, subsequent operations such as the reagent dispensations will not be carried out. If an abnormality occurred in the last reagent dispensation, the analysis will be carried out but an alarm indicating the analysis process abnormality will be attached to the measurement item and displayed. The automatic analyzer includes a mechanism for judging whether to carry out the subsequent steps if an abnormality has been detected in a step in the early stage of the analysis process and a mechanism for displaying the result of the judgment. The overall judgment is conducted as described above.

In the above analysis process, the pressure data judged to be abnormal is stored in a storage device. Such pressure data judged to be abnormal are stored for a long period and accumulated in regard to each data alarm. From the accumulated data, the difference between the measured pressure waveform and the approximation formula is calculated in each time domain and the abnormal pressure pattern is stored in the database together with a comment.

In cases of actual products, in order to detect an abnormality in the sample suction/discharge processes and the reagent suction/discharge processes, after the detection parameters are selected in advance and necessary values such as the permissible ranges are also determined and set to the automatic analyzer beforehand, the patient sample is analyzed. This procedure enables a previous investigation time for the determination of the parameters and the abnormality detection and the issuance of the alarm in the middle of the analysis process.

The first embodiment of the present invention will now be explained more concretely below.

Figure 5:
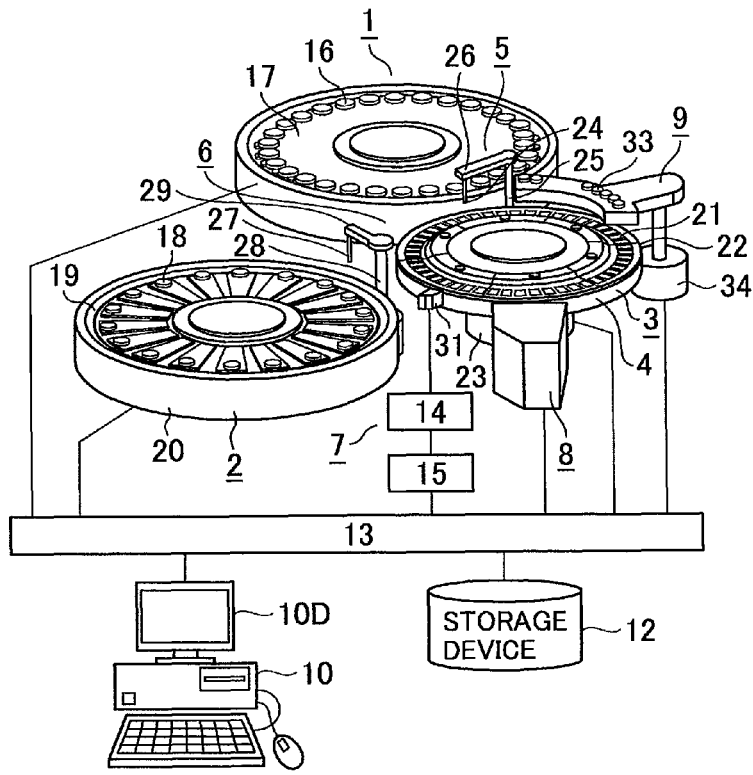
FIG. 5 is a schematic diagram showing the overall configuration of an automatic analyzer to which the present invention is applied.

FIG. 5 is a schematic diagram showing the overall configuration of a biochemical automatic analyzer to which the present invention is applied. In FIG. 5, the automatic analyzer includes a sampling disk 1, a reagent disk 2, a reaction disk 3, an incubation bath 4, a sampling mechanism 5, a pipetting mechanism 6, a stirring mechanism 7 (a stirring mechanism fixation part 31, a piezoelectric actuator 14, and a stirring controller 15), a photometric system 8, and a washing mechanism 9.

The automatic analyzer further includes a computer (arithmetic processing unit) 10, a storage device 12, a controlling unit 13, sample containers 16 storing samples, circular disks 17 and 19, reagent bottles (reagent storage) 18 storing reagents, a cooling unit 20, reaction cuvettes 21, a reaction cuvette holder 22, and a driver 23.

The automatic analyzer further includes dispensation probes 24 and 27, support shafts 25 and 28, arms 26 and 29, a nozzle 33, and a vertical driver 34.

The storage device 12 stores the analysis parameters, the possible number of times of analysis of each reagent bottle 18, the maximum possible number of times of analysis, calibration results, analysis results, and other information.

A sample is analyzed in the order of sampling, reagent dispensation, stirring, photometric measurement, cleaning reaction cuvette, and data processing including concentration conversion as will be explained below.

The sampling disk 1 is controlled by the controlling unit (analysis unit) 13 via the computer 10. A plurality of sample containers 16 are arranged circumferentially on the sampling disk 1. The sample containers 16 are moved to a position for the suction by the sample probe 24 in accordance with the order of samples to be analyzed. A prescribed amount of sample in the sample container 16 is dispensed into a reaction cuvette 21 by a sample pump (not shown) which is connected to the sampling mechanism 5.

The reaction cuvette 21 to which the sample has been dispensed moves in the incubation bath 4 to a first reagent addition position. To the reaction cuvette 21 which has moved to the first reagent addition position, a prescribed amount of first reagent sucked in from a reagent bottle (vessel) 18 by a reagent pump (not shown) connected to the reagent probe 27 is added. The reaction cuvette 21 after the addition of the first reagent moves to the position of the fixation part 31 of the stirring mechanism 7, where the first stirring is performed.

Such addition and stirring of a reagent is carried out for the first through fourth reagents, for example.

The reaction cuvette 21 after undergoing the stirring of its contents passes through a light beam emitted from a light source of the photometric system 8 and the absorbance at the time of the passage is then detected by the photometric system 8 serving as a multi-wavelength photometer. A signal representing the absorbance detected by the photometric system 8 is input to the controlling unit 13 and converted into the concentration of the analyte (sample). At the same time, the controlling unit 13 also makes an abnormality judgment on the analyte (sample) based on the absorbance.

The data converted into the concentration of the analyte is stored in the storage device 12 and displayed on a display unit 10D attached to the computer 10. The reaction cuvette 21 after the photometric measurement moves to the position of the washing mechanism 9, undergoes the cleaning by the washing mechanism 9, and is used for a subsequent analysis.

The computer 10 includes a keyboard and a CRT (display unit) 10D, for example, with which information on the analyte and measurement items are registered and the analysis parameters are set. The storage device 12 in advance stores the analysis parameters, a judgment process for evaluating the dispensation operation, data necessary for the judgment, and other elements. These data may either be stored in a storage medium attached to the computer 10 or exist separately as an individual storage database like the way of the storage device 12.

Figure 6:
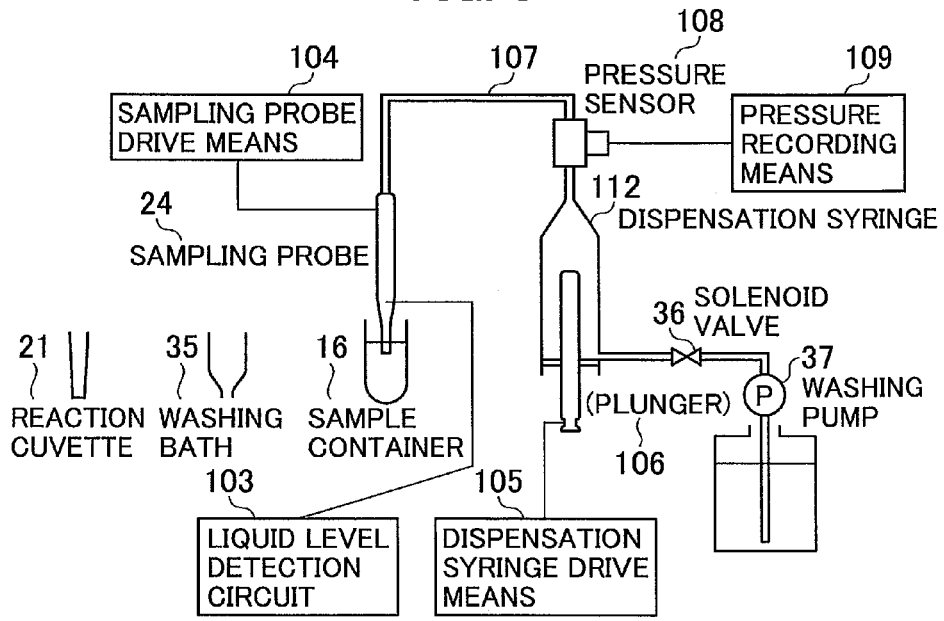
FIG. 6 is a schematic diagram showing the overall configuration of a sample dispensation mechanism of the automatic analyzer.

FIG. 6 is a schematic diagram for explaining the sample dispensation mechanism. In FIG. 6, accompanying intermittent rotation of the sampling disk 1, a sample container 16 is transferred to a sample suction position and the sample dispensation probe 24 descends to the inside of the sample container 16 stopped at the sample suction position. When the tip end of the descending dispensation probe 24 makes a contact with the liquid surface of the sample, a detection signal is output from a liquid level detection circuit 103. In accordance with the detection signal, the computer 10 executes the control to stop the lowering operation of a driver 104 of the sampling arm 26.

Subsequently, in order to suck in a prescribed amount of sample, a plunger 106 is operated by a dispensation syringe driver 105. After sucking in the prescribed amount of sample, the sample dispensation probe 24 rises to a top dead point. During the suction of the prescribed amount of sample by the sample dispensation probe 24, pressure fluctuation in the suction operation in a channel between the sample dispensation probe 24 and a sample pump channel 107 is monitored by a pressure recording mechanism (pressure measurement unit) 109 by use of a signal from a pressure sensor 108.

Subsequently, the sampling arm 26 rotates horizontally and lowers the sample dispensation probe 24 at the position of a reaction cuvette 21 on the reaction disk 3. Then, the sample dispensation probe 24 discharges the sample held therein into the reaction cuvette 21. The reagent pipetting mechanism 6 also operates in a similar manner. When the reaction cuvette 21 containing the sample has been moved to the reagent addition position, a reagent corresponding to the analysis item concerned is added to the reaction cuvette 21 from the reagent probe 27. Along with the dispensation of the sample and the reagent, the sample liquid level in the sample container 16 and the reagent liquid level in the reagent bottle 18 are detected.

It should be noted that the reference character "35" represents a cleaning bath of the washing mechanism 9 and the reference character "112" represents a dispensation syringe. The dispensation syringe 112 is connected to the pump channel 107. The dispensation syringe 112 is connected also to a cleaning pump 37 via a solenoid valve 36. The cleaning pump 37 sends a cleaning liquid stored in a cleaning bottle to the dispensation syringe 112.

While the configuration of the sample dispensation mechanism is shown in FIG. 6, the reagent dispensation mechanism is also configured in the same way. Specifically, the reagent dispensation mechanism is formed by replacing the sample probe 24, the sample probe driver 104 and the sample container 16 in FIG. 6 with the reagent probe 27, a reagent probe driver and the reagent bottle (vessel) 18, respectively.

Figure 13:
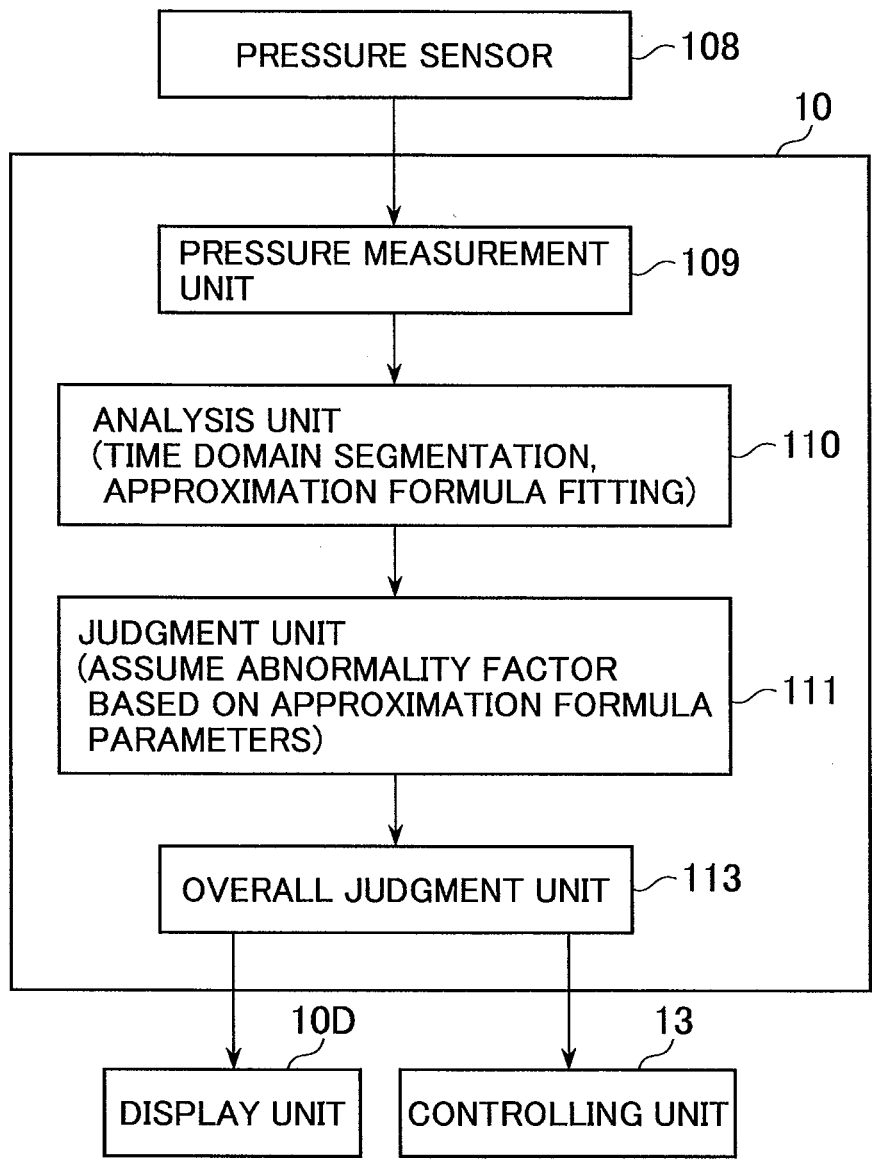
FIG. 13 is a functional block diagram showing an operation in the first embodiment of the present invention.

FIG. 13 is a functional block diagram of the computer 10. In FIG. 13, the computer 10 includes a pressure measurement unit 109, an analysis unit 110, a judgment unit 111, and an overall judgment unit 113.

A method and system for detecting a dispensation abnormality based on information obtained in the above dispensation operation process will now be explained below.

Figure 7:
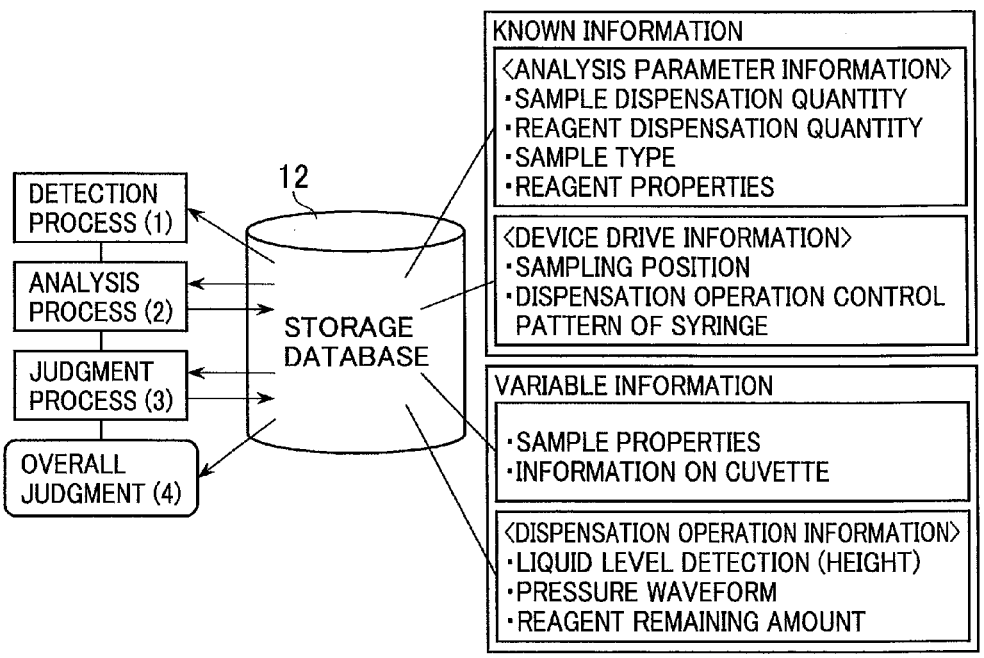
FIG. 7 is a schematic diagram for explaining a database which is stored in a storage device and used for a dispensation operation judgment.
Figure 8:
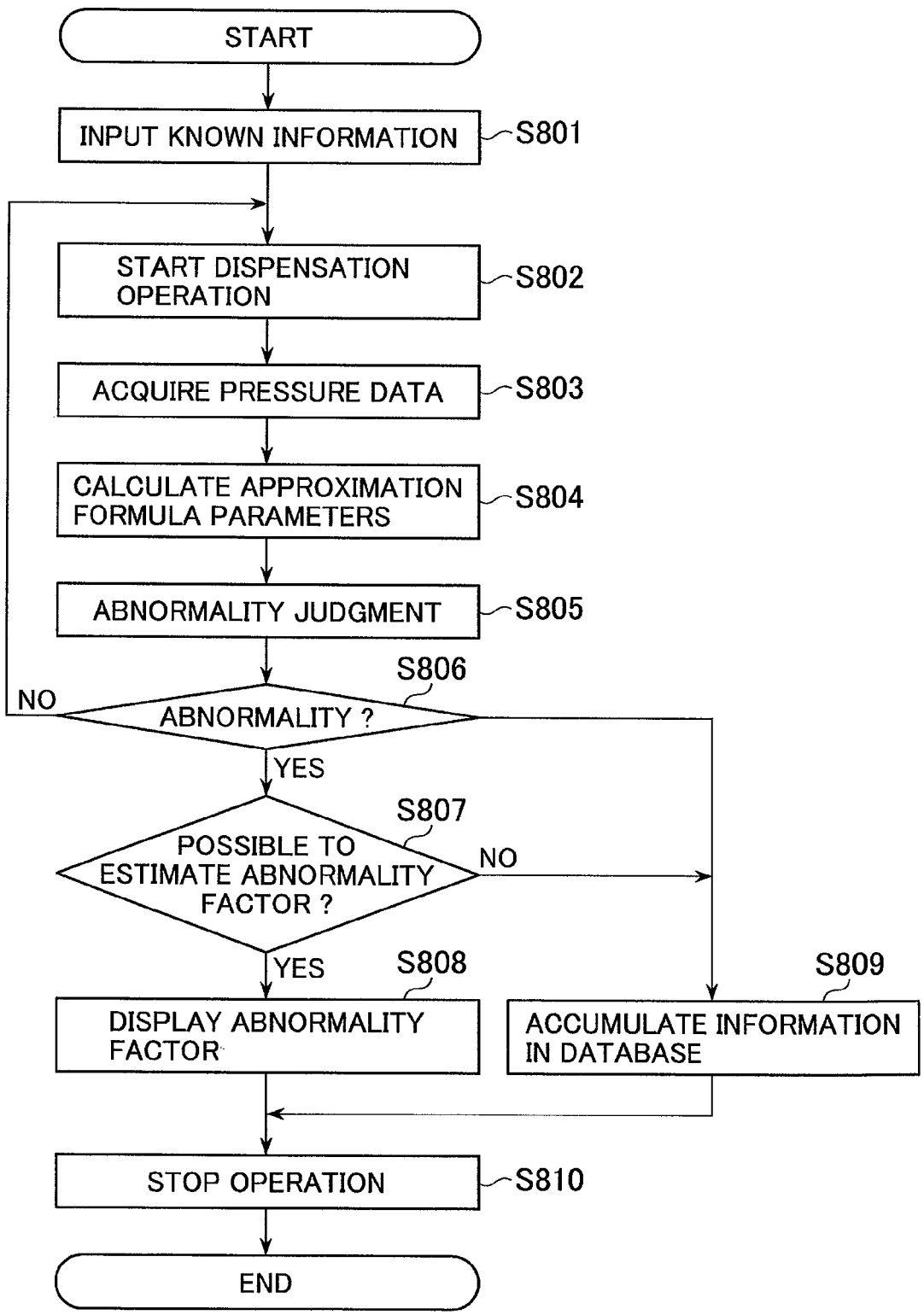
FIG. 8 is a flow chart of abnormality judgment in a first embodiment of the present invention.

FIG. 8 is a flow chart of the dispensation abnormality detecting operation. FIG. 7 is a schematic diagram showing the contents of a storage database stored in the storage device 12.

In step S801 in FIG. 8, the known information is input and stored in the storage device 12. As shown in FIG. 7, analysis parameter information (sample dispensation quantity, reagent dispensation quantity, sample type, and reagent properties) and device drive information (sampling position and dispensation operation control pattern of the syringe), which are already clearly known as the known information, are stored in the storage device 12 as a storage database. The sample type can be urine, serum, or whole blood. The reagent properties include the viscosity of the reagent and the presence/absence of a surface active agent.

These items of information can also be stored as parameter information before start of the analysis by manual input by the user via the computer 10. The sample types and/or the dispensation quantities can also be stored by manual input by the user via the computer 10. The sampling position or the reagent suction position can be determined from the relationship between the dispensation quantity and the liquid level height recorded in the automatic analyzer once the dispensation quantity is determined. In regard to the reagent properties, information previously supplied from the reagent manufacturer is input and stored. Further, the control pattern of the dispensation operation (suction and discharge) of the syringe, suction start time, driving speed, end time, and other information are also stored as parameters in the database of the storage device 12.

Meanwhile, information acquired after starting the analysis, such as the sample quantity and the reagent quantity of the analysis item and information obtained from the processes (the lowering, elevation and rotation of the probe and the suction and discharge operations of the syringe) during the dispensation operation (the information including liquid level height obtained by the liquid surface detection, as well as in-tube pressure change waveform), is recorded as the variable information in the storage database of the storage device 12. Further, sample properties, reagent remaining amount, sample container shape, and other information are also recorded in the storage database of the storage device 12.

At the start of the dispensation operation (step S802), the suction and discharge operations of the dispensation syringe 112 and the pressure around the times of the suction and the discharge are measured at certain time intervals by the pressure measurement unit 109 by use of the pressure sensor 108 arranged in the middle of the channel 107 connecting the dispensation syringe 112 and the sample dispensation probe 24 before the measurement data are stored in the database of the storage device 12 (step S803).

Thereafter, in the dispensation of the sample and the reagent, the pressure data of the pressure in the channel is analyzed by the analysis unit 110 on the basis of the aforementioned known information, data analysis of the variable information is performed, and then abnormality analysis of the suction and dispensation operations is conducted. The following process is performed for the analysis of the pressure waveform:

The analysis unit 110 segments the operation process of the syringe, used for the suction and discharge, into the four sections (a) to (d) as shown in FIG. 1.

Then, the analysis unit 110 conducts the analysis in each time domain by performing the approximation calculation on the pressure waveform by use of the aforementioned three types of formulas ($\alpha$) to ($\gamma$). In regard to each time domain, the analysis unit 110 calculates the parameters of the obtained approximation formula (step S804).

Subsequently, the judgment unit 111 judges whether the pressure waveform (data) is abnormal based on the parameters calculated by the applying to the approximation formula (step S805). The judgment on whether the data is abnormal is made as follows: Data in normal cases and data in abnormal cases are collected in advance and a pressure value in a normal case is determined by employing an approximation formula and multiple regression. Subsequently, approximation formula parameters in normal cases and those in abnormal cases are plotted on a graph and parameter values existing outside the range of normal cases are judged to be abnormal.

In step S806, if there is no abnormality, the process advances to the next dispensation operation (i.e., returns to the step S802).

If there is an abnormality in the step S806, a factor of the abnormality is assumed.

In this case, abnormality information is accumulated in the database of the storage device 12 (step S809). In step S807, whether an abnormality factor can be estimated is judged.

The parameters calculated for each approximation formula in the analysis process are utilized for the estimation of the abnormality factor. The above-described parameter check is conducted in the four time domains determined by the segmentation of the suction/discharge process, that is, in the total of eight time domains determined by the segmentation of the processes.

If an abnormality factor is estimated in the step S807, the abnormality factor is displayed on the screen of the PC 10 or the like (step S808) and the dispensation operation is stopped (step S810). If no abnormality factor can be estimated in the step S807, the process advances to the step S809.

In cases where the abnormality judgment on the syringe is made in each time domain by calculating the difference between the measured pressure waveform and the approximation formula, the abnormal pressure pattern under consideration will be stored with a comment in the database of the storage device 12.

When there exists an abnormality other than estimated causes, values of the pressure waveform, values of the calculated parameters, and the known information are stored as a combination in the database of the storage device 12.

The above abnormality judgment process is conducted for each process (sample dispensation [sampling], reagent dispensation, etc.) in the order of the sampling, the first reagent dispensation and the second reagent dispensation. If an abnormality has been detected in an early stage of the analysis process, the subsequent measurement operation will not be carried out. An alarm indicating the abnormality is displayed on the screen of the PC 10 at the stage when the measurement operation is stopped, or added to the data as a comment.

Figure 9:
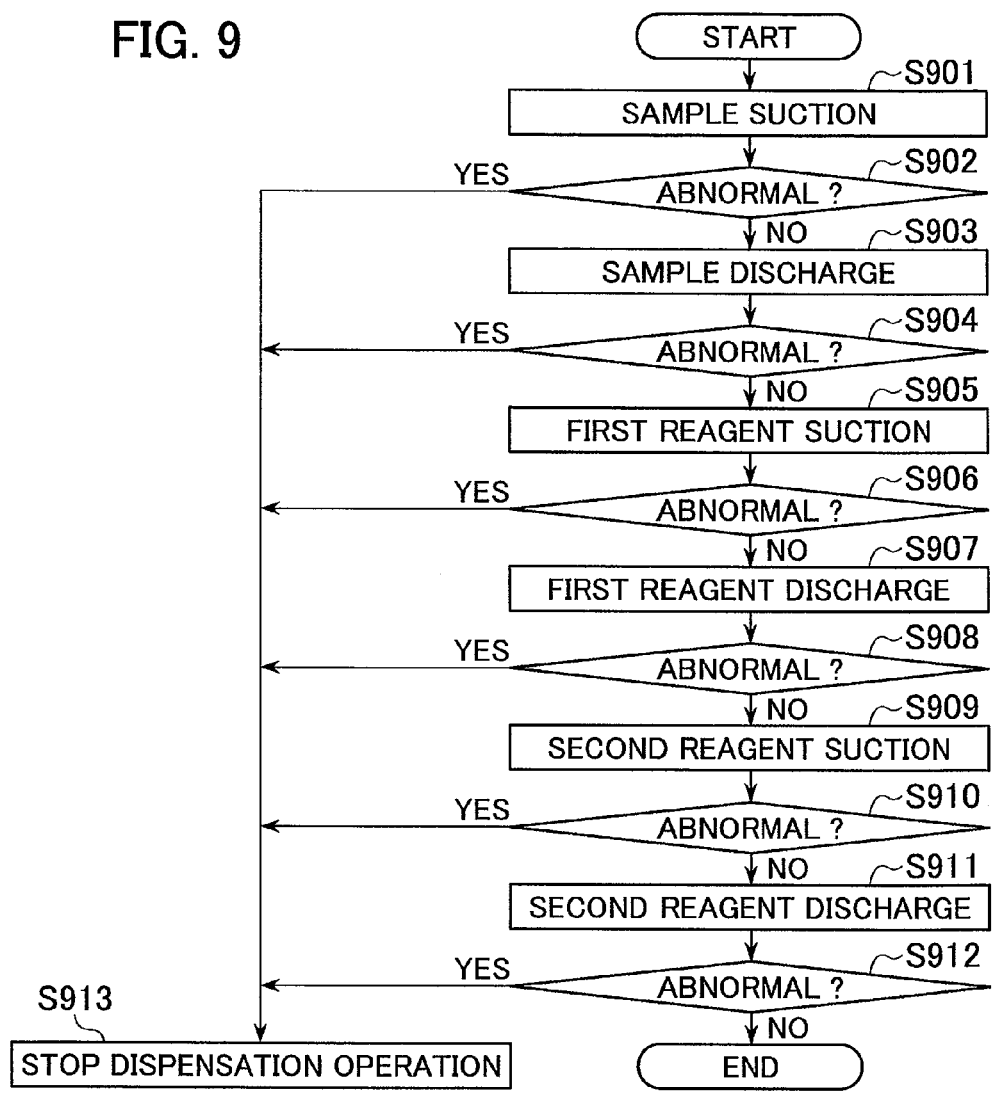
FIG. 9 is a flow chart of overall judgment in the first embodiment of the present invention.

FIG. 9 is an analysis operation flow chart of the overall judgment process executed by the overall judgment unit 113. In FIG. 9, according to the order of analysis operations, the sample suction (step S901) is conducted first, in which an abnormality judgment at the time of suction is made (step S902). If the sample suction is judged to be abnormal in the step S902, the dispensation operation is stopped (step S913).

If the sample suction is judged to be normal in the step S902, the process advances to the next sample discharge operation (step S903). In the sample discharge operation, an abnormality judgment at the time of sample discharge (step S904) is made and if the sample discharge is judged to be abnormal, the analysis operation is stopped (step S913). If the sample discharge is judged to be normal in the step S904, the first reagent suction (step S905) is performed and an abnormality judgment is made (step S906).

Thereafter, an abnormality judgment is made in each of the discharge of the first reagent, the suction of the second reagent and the discharge of the second reagent (steps S907 to 912).

As above, the abnormality judgment process is conducted successively for the six dispensation operations (from the suction and discharge of the sample to the suction and discharge of the second reagent) concurrently with each dispensation operation (steps S5901 to S913). After a stop command is sent from the overall judgment unit 113 to the controlling unit 13 and the dispensation operation is stopped, if the sample or the reagent has already been sucked into the dispensation probe 24 or 27, the dispensation probe 24 or 27 may be cleaned after dispensation to the reaction cuvette 21. It is also possible to return the solution (sample/reagent) to the sample container 16 or the reagent bottle 18 without dispensing the sample/reagent to the reaction cuvette 21, or to transfer the sample dispensation probe 24 or the reagent probe 27 (still filled with the sucked solution) to the cleaning bath 35 and carry out the discharge and the cleaning in the cleaning bath 35.

In cases where an abnormality factor of the suction/discharge abnormality has been estimated, it would be preferable to display the abnormality factor as an alarm on the display unit 10D attached to the computer 10. Even when no factor of the abnormality can be estimated, if the dispensation was different from normal dispensation, an alarm is displayed or a comment is stored in the computer 10. Based on the accumulated information, it is possible to newly detect characteristic patterns. It would also be possible to construct a judgment process as a new abnormality judgment point in cases where multiple abnormalities have occurred.

Here, the parameter determination work which is conducted previously will be explained briefly.

For the pressure abnormality judgment, an analysis operation is performed by use of multiple patient samples and a reagent. In this case, a previous analysis is conducted by measuring the pressure of abnormal dispensation or normal dispensation. It is necessary to determine a normal permissible range, abnormal ranges, etc. The permissible range is determined by performing multivariate analysis on parameters calculated in multiple processes. Techniques such as principal component analysis are used. The result is compared with evaluations (normal or abnormal) of multiple patients' data, and the most reliable numerical values, based on whether the judgment was made correctly or the number of erroneous judgment results, are used.

In cases of actual products, in order to detect an abnormality in the sample suction/discharge processes and the reagent suction/discharge processes, the detection parameters are in advance set at optimum values for each analysis item differing in the sample quantity and the reagent quantity. Necessary values such as the permissible ranges are also previously determined and set to the automatic analyzer, after which the patient sample is analyzed. This previous work enables a previous investigation time for the determination of the parameters and the abnormality detection and the issuance of the alarm in the middle of the analysis process.

A method for the judgment on the dispensation operation will now be explained in detail below by taking the sample dispensation as an example.

Figure 10:
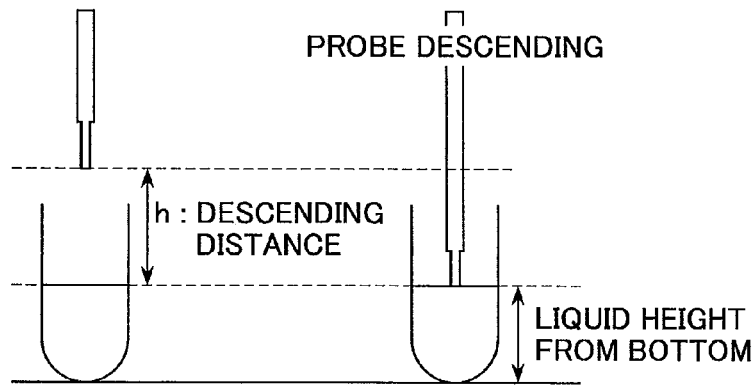
FIG. 10 is a schematic diagram for explaining descending distance of a probe.

First, in the pressure measurement process (1), a check is conducted based on the information acquired from the detector including pressure sensor and liquid level detector. For example, as shown in FIG. 10, detecting the descending distance of the probe from its fixation position to the liquid surface calculates the height of the liquid surface by means of liquid level detection. Based on the information on the descending distance h and the type of the sample container, the liquid level height from the bottom of the sample container can be calculated and a part in the pressure waveform acquired by the pressure sensor and influenced by the height can be inferred.

In the next analysis process (2), a check based on basic information including dispensation quantity and syringe operation time is conducted. A syringe driving time and a suction relaxation time can be determined from the pressure waveform. These times should be constant as long as the dispensation quantity is constant.

However, when a sample having high viscosity is sucked in, for example, bubbles can form and the discharge quantity could be decreased by the bubbles. Accordingly, the discharge quantity can be estimated from the length of this response time.

In the judgment process (3), it is possible to estimate a pressure waveform pattern that is roughly determined from the abnormality factor, such as high viscosity and height abnormality, estimated to some extent by the pressure measurement process (1) and the analysis process (2). A pattern comparison is made between the estimated pressure waveform and the actual pressure waveform by means of multivariate analysis (e.g., Mahalanobis distance). As a result of the comparison between the estimated waveform and the actual waveform, the difference between these waveforms is extracted in the pressure measurement process (1) and the analysis process (2).

The result of the judgment process (3) is displayed as an alarm together with the estimated abnormality factor, the estimated dispensation quantity, and other information. In regard to dispensation not reaching the determination of the abnormality factor but having a pattern different from those of normal waveforms, the data is stored as information in the automatic analyzer. The stored information may be used by a serviceperson in the periodic maintenance as verification data regarding the dispensation mechanism. The automatic analyzer may be equipped with a display function that calls for users' attention by adding a comment, for example, to the measurement result.

A method for judging each assumed abnormality factor will now be explained below.

(1) Possibility of Clogging or Bubbles

The sample suction height shown in FIG. 10 varies depending on the type of the sample container and the volume of the sample. The sample suction height influences the pressure values detected by the pressure sensor at the time of driving the syringe. A change in the sample suction height causes a change in the value of the base of the pressure waveform. There is a linear correlation between the suction height and the pressure value.

Therefore, when the height from the bottom of the sample container and the pressure value in the channel (obtained from the actual dispensation operation) deviate from the above correlation, the possibility of having incorrectly recognized the liquid surface (due to bubbles or the like) and failed to correctly sucking in the intended dispensation quantity can be inferred.

(2) Viscosity of Sample

FIG. 11 is a graph showing pressure waveforms varying depending on the viscosity of the sample.

The viscosity of the sample varies from sample to sample and cannot be learned previously. However, it is clear as shown in FIG. 11 that the pressure waveform obtained from the pressure sensor in the syringe driving period varies in shape depending on the viscosity of the sample.

The four patterns of pressure waveform data S111 to S114 shown in FIG. 11 were obtained when samples differing in the viscosity were sucked in. The waveform patterns S111, S112, S113 and S114 were obtained with the increase in the sample viscosity (the waveform pattern S111 was obtained when the sample of the lowest viscosity was sucked in).

As shown in FIG. 11, the shape of the pressure waveform just after the suction varies depending on the sample viscosity. In the section S115, for example, when the viscosity is high, the fluctuation in the pressure value due to the damped oscillation after the start of the syringe operation is lower in comparison with the low viscosity examples. This is because the influence of the oscillation of the syringe on the waveform change decreases with the increase in the viscosity.

Further, the pressure value itself at the time point S116 also changes (increases in the absolute value) with the increase in the viscosity. By use of these feature values, correlation between the viscosity and the pressure value (or the pressure waveform shape) can be determined. Based on the correlation, the viscosity of the sample can be estimated from the pressure value or the pressure waveform obtained when the sample was actually dispensed.

The viscosity of serum is generally 1.0 to 1.8 mPa·s. When the calculated value of the viscosity is 2.0 mPa·s or higher, for example, the amount of the sample discharged to the reaction cuvette can become less than the preset amount (if the syringe is driven at the same speed) since the shear rate generally decreases with the increase in the viscosity of the solution.

(3) Judgment on Sample Dispensation Quantity

The dispensation quantity has previously been set as a parameter. Based on the preset dispensation quantity, the length of the time for performing the suction operation by driving the syringe has been determined from a control parameter in the automatic analyzer.

FIGS. 12A and 12B are graphs showing a change in the behavior pattern of the pressure waveform depending on the dispensation quantity.

As shown in FIGS. 12A and 12B, the behavior pattern of the pressure waveform at the time of sample suction varies depending on the dispensation quantity. The suction operation time and the suction relaxation time (in which the pressure after the end of the suction returns to the original level) vary depending on the dispensation quantity. These times have correlation with the actual suction quantity.

Accordingly, when the actual waveform differs from the waveform pattern assumed from the dispensation quantity which has been set by an analysis parameter, the dispensation can be evaluated to have failed in the suction of the correct quantity. It is also possible to estimate the actual suction quantity from the waveform.

The correlations between the suction height, the viscosity or the dispensation quantity and the pressure value or the pressure waveform obtained from the above (1) Possibility of clogging or bubbles, (2) Viscosity of sample and (3) Judgment on sample dispensation quantity are previously stored in the database of the storage device 12 as reference values for the abnormality judgment. Not only the data at the time of suction but also the pressure waveform at the time of discharge can be similarly used for the judgment on the abnormality factors (1) to (3). It is possible either to use only the data at the time of suction or discharge or to use both of the data at the times of suction and discharge. From the pressure waveform pattern obtained in the actual dispensation of the sample, characteristic patterns of the abnormality factors (1) to (3) are extracted and analyzed.

The analysis may be conducted as follows: A reference value may be set in cases where a pressure value has already been determined. In regard to two types of data having correlation and allowing for the calculation of a regression line, data deviating a certain distance or more from the regression line may be judged to be abnormal, the data being exemplified by the pressure value and the suction height. In regard to a feature that cannot be represented by numerical values (e.g., waveform shape), it is possible to set feature values in detail and detect an abnormal pattern by use of the Mahalanobis distance or the like.

In the first embodiment of the present invention, the sample/reagent suction and discharge operation time of the dispensation probe 24 and 27 is segmented into multiple times (time sections). For each time section determined by the segmentation, parameters are calculated by applying the detected pressure waveform to an approximation formula. Then, a judgment on the presence/absence of a dispensation abnormality is made for each time section by comparing the calculated parameters with the parameters in cases of normal dispensation. In this case, the known information and the variable information can be used as references for the setting of the normal parameters.

Therefore, the automatic analyzer and the dispensation abnormality judgment method capable of judging the presence/absence of an abnormality specific to each time section and making abnormality judgments difficult with conventional techniques can be realized.

Second Embodiment

In the dispensation operation judgment method in the first embodiment of the present invention, each of the pressure changes in the dispensation and the discharge of the sample is segmented into four processes (the pressure measurement process, the analysis process, the judgment process and the overall judgment process). For the pressure change in each process, the analysis is made by applying an approximation formula to the pressure change. From the parameters of the approximation formula, an abnormality in the process is detected. A judgment as the combination of the above processes is carried out as the overall judgment, which is based on the abnormality detection in each process.

There exists a method different from that of the first embodiment of the present invention, such as a method of making the overall judgment in a statistical and mathematical manner based on multiple items of data.

The second embodiment of the present invention employs the above method of making the overall judgment in a statistical and mathematical manner based on multiple items of data. In this embodiment, parameter extraction from the formula used in each of the above processes, normalization of the extracted parameters, and principal component analysis based on the normalized parameters of each process are conducted. Since the overall configuration of the automatic analyzer in the second embodiment is equivalent to that shown in FIG. 5 and the rest of the configuration is also substantially equivalent to that in the first embodiment, the detailed explanation thereof is omitted for brevity.

The judgment on the suction/discharge abnormality of the dispensation probe is made by generating a formula of each principal component in the second embodiment. The flow of the judgment will be explained below.

(1) Application of Approximation Formula to each Process

An approximation formula is generated by applying a damped oscillation function, an increasing function, or other functions to the pressure change in each process. In cases where only the magnitude of the pressure is necessary, a simple check of the pressure value would be conducted.

(2) Parameter Extraction

A parameter that most reflects the fluctuation in the process under consideration is extracted.

In multiple pieces of pressure change data, each parameter of each process is digitized by classifying the parameter into multiple levels (e.g., 10 levels). In the case of pressure, the maximum value and the minimum value in the distribution of the multiple pieces of data are respectively digitized to 10 and 0. When the exponential function shown in ($\alpha$) in the first embodiment is used, the maximum value 10 and the minimum value 0 are prescribed based on the distribution of the parameter k. Similarly, multiple pieces of data are normalized in each process.

Table 2 shows an example of parameters normalized in each time domain (a) to (d) and in regard to each piece of sampling data.

TABLE 2

| DATA | NORMALIZED PARAMETERS IN EACH TIME DOMAIN | | | |
|---|---|---|---|---|
| | (a) | (b) | (c) | (d) |
| SAMPLING DATA 1 | 0 | 1 | 2 | 1 |
| SAMPLING DATA 2 | 1 | 1 | 2 | 1 |
| SAMPLING DATA 3 | 3 | 3 | 3 | 2 |
| SAMPLING DATA 4 | 0 | 5 | 2 | 3 |
| SAMPLING DATA 5 | 1 | 5 | 4 | 3 |
| . | | | | |
| . | | | | |
| SAMPLING DATA 6 | | | | |

(3) Principal Component Analysis

The principal component analysis is conducted by use of the multiple pieces of normalized data. Since the pressure process is segmented into four processes in this second embodiment, up to four components can be calculated in the principal component analysis.

(4) Application to Patient Sample

The normalized parameters obtained by analyzing the pressure change at the time of sample measurement are applied to the formula of each principal component calculated by the principal component analysis. In regard to each principal component, a dispensation abnormality is detected by the applying to the liquid level height, the sample viscosity, influence of accuracy, etc.

As described above, the automatic analyzers according to the first and second embodiments of the present invention make it possible to detect not only clogging and air suction of the dispensation probe but also a decrease in the dispensation quantity caused by a bubble film, air bubbles or a highly viscous sample, and to check whether the dispensation of a sample or reagent has been performed appropriately. Further, the cause of the abnormality can be inferred by the overall judgment.

Furthermore, it becomes possible to evaluate whether the actual dispensation has been performed appropriately and the preset target quantity has been sucked in. It is also possible to evaluate whether the prescribed quantity has been discharged to the reaction cuvette. These processes increase the reliability of the dispensation mechanism of the automatic analyzer and the reliability of obtained measurement results.

In the present invention, the abnormality factor can be estimated by evaluating and analyzing the obtained information in an integrated manner. While the issuance of a simple alarm of a dispensation abnormality works fine to inform a clinical technologist that the dispensation was abnormal, the determination of the factor of the abnormality takes a long time. Once the factor is determined, the clinical technologist in charge of the automatic analyzer can immediately eliminate the factor and start a correct measurement. Therefore, the present invention contributes not only to the increase in the reliability of data but also to a reduction in the load on clinical technologists.

DESCRIPTION OF REFERENCE CHARACTERS 1 sampling disk
2 reagent disk
3 reaction disk
4 incubation bath
5 sampling mechanism
6 pipetting mechanism
7 stirring mechanism
8 photometric system
9 washing mechanism
10 computer (PC)
10D display unit
12 storage device
13 controlling unit
14 piezoelectric actuator
15 stirring controller
16 sample container
17, 19 circular disk
18 reagent bottle
20 cooling unit
21 reaction cuvette
22 reaction cuvette holder
23 driver
24 sample dispensation probe
25, 28 support shaft
26, 29 arm
27 reagent probe
31 fixation part
33 nozzle
34 vertical driver
103 liquid level detection circuit
104 sample probe driver
105 dispensation syringe drive means
106 plunger
107 sample pump channel
108 pressure sensor
109 pressure measurement unit

The invention claimed is:

1. An automatic analyzer comprising:
a dispensation probe which sucks in a sample or a reagent stored in a sample container or a reagent bottle and discharges the sample or reagent to a reaction cuvette;
a pressure detector which detects a pressure in the dispensation probe;
an analyzer which analyzes the sample in the reaction cuvette;
a storage unit which stores information on a type of the sample, a sampling position, a dispensation quantity, and viscosity and composition of the reagent as known information, a computer including a processor and a memory storing instructions that when executed by the processor cause the processor to:

segment each of the suction operation and the discharge operation of the dispensation probe into multiple time sections, wherein the time sections determined by the segmentation by the arithmetic processing unit are: a time from a point just after the start of operation of a syringe performing the dispensation probe's suction and discharge operation till the syringe reaches a constant speed; a time during which the syringe maintains the constant speed; a time from a point when the operation speed of the syringe starts decreasing to a point when the syringe stops; and a certain length of time after the stoppage of the operation of the syringe, the above time sections being set on the basis of the known information stored in the storage unit, analyze a pressure waveform detected by the pressure detector in regard to each of the time sections determined by the segmentation, and judge presence/absence of a dispensation abnormality by comparing a result of the analysis of the pressure waveform with a certain criterion; and a display unit which displays the presence/absence of the dispensation abnormality as a result of the judgment executed by the processor.

2. The automatic analyzer according to claim 1, wherein the execution of the instructions by the processor further causes the processor to approximate the pressure waveform in each of the time sections by use of an approximation formula in which the pressure increases with passage of time, a damped oscillation function approximation formula and/or an approximation formula for judging a certain pressure, and judges the presence/absence of a dispensation abnormality by comparing a parameter of an approximation formula determined by the approximation with previously determined parameter in regard to each of the time sections.

3. The automatic analyzer according to claim 2, wherein the execution of the instructions by the processor further causes the processor to:

in the time section from the point just after the start of the operation of the syringe till the syringe reaches the constant speed, approximate the pressure waveform by use of an exponential function approximation formula and judges viscosity of the sample based on a parameter of the exponential function approximation formula determined by the approximation, in the time section during which the syringe maintains the constant speed, approximate the pressure waveform by use of an exponential function approximation formula and judges sample suction height of the dispensation probe based on a parameter of the exponential function approximation formula determined by the approximation and magnitude of the detected pressure, in the time section from the point when the operation speed of the syringe starts decreasing to the point when the syringe stops, approximate the pressure waveform by use of an exponential function approximation formula and judges clogging of the dispensation probe with the sample based on a parameter of the exponential function approximation formula determined by the approximation, and in the certain length of time section after the stoppage of the operation of the syringe, approximate the pressure waveform by use of a damped oscillation function approximation formula and judge sample suction quantity or discharge quantity of the dispensation probe based on a frequency as a parameter of the damped oscillation function approximation formula determined by the approximation.

4. The automatic analyzer according to claim 3, wherein the execution of the instructions by the processor further causes the processor to:

make the judgment on the presence/absence of a dispensation operation abnormality of the dispensation probe in each of a sample suction process, a sample discharge process, a suction discharge process of a first reagent, a suction discharge process of a second reagent and a suction discharge process of a third reagent, and stop subsequent dispensation operation or makes the display unit display an abnormality alarm at the point when the dispensation abnormality is detected.

5. A method of judging dispensation abnormality of an automatic analyzer, the method comprising the steps of:

sucking in a sample or a reagent stored in a sample container or a reagent bottle and discharging the sample or reagent to a reaction cuvette by use of a dispensation probe;

detecting the pressure in the dispensation probe by use of a pressure detector;

executing instructions by a computer having a processor to segment each of the suction operation and the discharge operation of the dispensation probe into multiple time sections, analyze a pressure waveform detected by the pressure detector in regard to each of the time sections determined by the segmentation, and judge the presence/absence of a dispensation abnormality by comparing the result of the analysis of the pressure waveform with a certain criterion; and displaying the presence/absence of a dispensation abnormality as the result of the judgment executed by the processor, wherein information on the type of the sample, a sampling position, a dispensation quantity, and viscosity and composition of the reagent is stored in a storage unit as known information, and wherein the time sections determined by the segmentation by the processor are: a time from a point just after the start of operation of a syringe performing the dispensation probe's suction and discharge operation till the syringe reaches a constant speed; a time during which the syringe maintains the constant speed; a time from a point when the operation speed of the syringe starts decreasing to a point when the syringe stops; and a certain length of time after the stoppage of the operation of the syringe, the above time sections being set on the basis of the known information stored in the storage unit.

6. The method for judging dispensation abnormality of an automatic analyzer according to claim 5, comprising:

a first process of judging an abnormality in the dispensation on the basis of the known information;

a second process of judging an abnormality in the dispensation on the basis of variable information detected by performing the dispensation operation;

a third process of judging an abnormality in the dispensation on the basis of the value of the pressure in the dispensation probe; and a fourth process of judging whether a cause of the abnormality is a single cause or a complex cause on the basis of the results of the judgments in the first process, the second process and the third process.

* * * * *